United States Patent
Gilbert (10) Patent No.: US 7,316,680 B2
(45) Date of Patent: Jan. 8, 2008

(54) OSMOTIC DELIVERY DEVICE HAVING A TWO-WAY VALVE AND A DYNAMICALLY SELF-ADJUSTING FLOW CHANNEL

(75) Inventor: Scott Jay Gilbert, Menlo Park, CA (US)

(73) Assignee: Intarcia Therapeutics, Inc., Emeryville, CA (US)

( * ) Notice: Subject to any disclaimer, the term of this patent is extended or adjusted under 35 U.S.C. 154(b) by 52 days.

(21) Appl. No.: 11/237,489

(22) Filed: Sep. 27, 2005

(65) Prior Publication Data

US 2006/0116665 A1    Jun. 1, 2006

Related U.S. Application Data

(62) Division of application No. 10/302,104, filed on Nov. 21, 2002, now Pat. No. 7,014,636.

(51) Int. Cl.
*A61K 9/22* (2006.01)
(52) U.S. Cl. .................................. 604/892.1
(58) Field of Classification Search ............. 251/12, 251/368, 111; 267/41; 604/892.1
See application file for complete search history.

(56) References Cited

U.S. PATENT DOCUMENTS

| | | | |
|---|---|---|---|
| 3,122,162 A * | 2/1964 | Sands | .......... 137/498 |
| 3,987,790 A | 10/1976 | Eckenhoff et al. | |
| 4,865,845 A | 9/1989 | Eckenhoff et al. | |
| 5,059,423 A | 10/1991 | Magruder et al. | |
| 5,112,614 A | 5/1992 | Magruder et al. | |
| 5,137,727 A | 8/1992 | Eckenhoff | |
| 5,213,809 A | 5/1993 | Wright et al. | |
| 5,221,278 A | 6/1993 | Linkwitz et al. | |
| 5,234,692 A | 8/1993 | Magruder et al. | |
| 5,234,693 A | 8/1993 | Magruder et al. | |
| 5,308,348 A | 5/1994 | Balaban et al. | |
| 5,413,572 A | 5/1995 | Wong et al. | |
| 5,514,110 A | 5/1996 | Teh | |
| 5,540,665 A | 7/1996 | Mercado et al. | |

(Continued)

FOREIGN PATENT DOCUMENTS

FR    640907    7/1928

(Continued)

OTHER PUBLICATIONS

Ann. Book of ASTM Stds., vol. 8.02, pp. 208-211 and pp. 584-587 (1984).

(Continued)

*Primary Examiner*—Kevin C. Sirmons
*Assistant Examiner*—Deanna Hall
(74) *Attorney, Agent, or Firm*—Trask Britt (57) ABSTRACT

An implantable osmotically driven delivery system having a dynamic, two-way valve and a self-adjusting, variable geometry fluid flow channel. As pressure within the agent delivery system increases, the fluid channel narrows, thereby restricting flow. At exceptionally high pressures, the valve can be designed to close altogether at the orifice or delivery end, or it can provide a minimal leak path so that a maximum fluid flow is never exceeded. At zero or very low pressures, the valve will close completely at the beneficial agent reservoir end, isolating the beneficial agent formulation from external fluid infiltration and thereby eliminating diffusion of external fluid into the beneficial agent formulation.

8 Claims, 4 Drawing Sheets

U.S. PATENT DOCUMENTS

| | | | |
|---|---|---|---|
| 5,728,396 A | 3/1998 | Peery et al. | |
| 5,985,305 A | 11/1999 | Peery et al. | |
| 5,997,527 A * | 12/1999 | Gumucio et al. | 604/892.1 |
| 6,183,461 B1 | 2/2001 | Matsuura et al. | |
| 6,270,787 B1 | 8/2001 | Ayer | |
| 6,508,808 B1 | 1/2003 | Carr et al. | |
| 6,835,194 B2 | 12/2004 | Johnson et al. | |
| 2003/0097121 A1 | 5/2003 | Jolly et al. | |

FOREIGN PATENT DOCUMENTS

| | | |
|---|---|---|
| WO | WO 97/47339 | 12/1997 |

OTHER PUBLICATIONS

Kildsig et al., "Theoretical Justification of Reciprocal Rate Plots in Studies of Water Vapor Transmission through Films," J. Pharm. Sci., vol. 29, pp. 1634-1637 (1970).

Mohler, J.B., "Primer on electrodeposited coatings," Materials Engineering, vol. 5, pp. 38-45 (1972).

Morgan, P.W., "Structure and Moisture Permeability of Film-Forming Polymers," Ind. and Eng. Chem., vol. 45, pp. 2296-2306 (1953).

Roff, et al., "Handbook of Common Polymers," CRC Press, Cleveland Rubber Co., Cleveland, Ohio (72 total pages) (1971).

Rogers et al., "Permeability Valves; Permeability of Gases and Vapors through Composite Membranes," Ind. and Eng. Chem., vol. 49, pp. 1933-1936 (1957).

International Search Report dated Aug. 7, 2003 (7 pages).

* cited by examiner

OSMOTIC DELIVERY DEVICE HAVING A TWO-WAY VALVE AND A DYNAMICALLY SELF-ADJUSTING FLOW CHANNEL

CROSS-REFERENCE TO RELATED APPLICATION

This application is a divisional of application Ser. No. 10/302,104, filed Nov. 21, 2002, now U.S. Pat. No. 7,014,636.

BACKGROUND OF THE INVENTION

1. Field of the Invention

The present invention pertains to osmotically controlled implantable delivery devices, and more particularly to a delivery device having a two-way miniature valve and a dynamically self-adjusting flow channel for the regulation of back-diffusion and fluid delivery rate in an osmotically driven delivery system.

2. Description of the Related Art

Controlled delivery of beneficial agents, such as drugs, in the medical and the veterinary fields has been accomplished by a variety of methods, including implantable delivery devices, such as implantable osmotic delivery devices. Osmotic delivery systems are very reliable in delivering a beneficial agent over an extended period of time, called an administration period. In general, osmotic delivery systems operate by imbibing fluid from an outside environment and releasing controlled amounts of beneficial agent from the delivery system.

Representative examples of various types of delivery devices are disclosed in U.S. Pat. Nos. 3,987,790; 4,865,845; 5,059,423; 5,112,614; 5,137,727; 5,213,809; 5,234,692; 5,234,693; 5,308,348; 5,413,572; 5,540,665; 5,728,396; 5,985,305; and 5,221,278, all of which are incorporated herein by reference. All of the above patents generally include some type of capsule having walls, or portions of walls (for example, semi-permeable membranes) that selectively pass water into the interior of the capsule. The absorption of water by a water-attracting agent contained within the capsule creates an osmotic pressure within the capsule, which then causes a beneficial agent within the capsule to be expelled. Alternatively, the water-attracting agent may be the beneficial agent being delivered to the patient. However, in most cases, a separate agent is used specifically for its ability to draw water into the capsule.

When a separate osmotic agent is used, the osmotic agent may be separated from the beneficial agent within the capsule by a movable dividing member such as a piston. The structure of the capsule is generally rigid such that as the osmotic agent takes in water and expands, the capsule itself does not expand. As the osmotic agent expands, the agent causes the movable dividing member to move, discharging the beneficial agent through an orifice or exit passage of the capsule. The beneficial agent is discharged through the exit passage at the same volumetric rate that water combines with the osmotic agent through the semi-permeable walls of the capsule.

In some known implantable delivery devices, the orifice or exit passage of the capsule is permanently open and thus allows for unimpeded discharge of the beneficial agent. This results in a direct fluid communication between the beneficial agent and water in the surrounding tissue of the patient. Thus, back-diffusion of the water into the beneficial agent reservoir may result. One way in which back-diffusion of water has been reduced is by providing a long orifice or exit passage that can be a variety of shapes, such as straight or spiral.

In other known implantable delivery devices, the orifice or exit passage of the capsule is covered with a stretchable or elastic member or band, to reduce back-diffusion of water into the beneficial agent reservoir. The stretchable or elastic band allows discharge of the beneficial agent once a threshold pressure has been overcome. The stretchable or elastic member or band closes the orifice when the pressure in the device is less than the threshold pressure. However, in these types of devices there is little or no control of the pressure that can build up as the device adjusts to changes in temperature and/or internal or external pressure.

In still other known implantable delivery devices, the orifice or exit passage is at least partially made of a stretchable or elastic material that acts to reduce back-diffusion of water into the beneficial agent reservoir. This stretchable or elastic material deforms once a threshold pressure has been achieved in the device to allow discharge of the beneficial agent. The stretchable orifice material closes when the internal pressure in the device is less than the threshold pressure. However, in these types of devices there is little or no control of the pressure that can build up as the device adjusts to changes in temperature and/or internal or external pressure.

In general, osmotic delivery systems rely on the flow of interstitial body fluid across a rate-limiting membrane (also known as a semi-permeable membrane) to drive the osmotic agent expansion that in turn drives the delivery or discharge of the beneficial agent. During the period immediately following implantation, this interstitial fluid may also diffuse into the beneficial agent via a beneficial agent delivery channel (also known as an orifice or exit passage). Such diffusion is undesirable because it results in an uncontrolled dilution of the beneficial agent formulation.

In those prior known designs which attempt to limit or prevent back-diffusion without covering the orifice or exit passage, one limitation has been that a relatively long diffusion path is required to prevent or impede back-diffusion of the fluid into the beneficial agent compartment. The long orifice, diffusion path, or exit channel in these known designs has been formed by molding intricate detail into plastic or by machining high tolerance surfaces into metal. These approaches are costly to manufacture and occupy a relatively large volume, causing the implant to have an increased size.

A further drawback of known implantable delivery devices is that these devices do not compensate for variations in temperature and internal pressure that can cause the implantable delivery device to deliver beneficial agent temporarily at high or low rates. Typically, an implantable, osmotically driven delivery system will have been stored at ambient room temperature (approximately 20 to 22° C.) prior to implantation into a patient. Within a few hours following implantation, the system will subsequently come to thermal equilibrium with the patient (approximately 37° C.). This increase in temperature may cause the beneficial agent formulation within the implantable device to expand, which may result in a pressurization of the system and a rapid, short-duration delivery of beneficial agent often referred to as a start-up "burst." This burst is typically followed by a short period of somewhat low agent delivery (typically lasting from less than one day to 5 days) during which time the osmotic pressure is increased to a degree equal to that of the piston friction. As the internal pressure of the implantable device increases, the rate of beneficial agent delivery will rise until it obtains a steady state. Since it is the purpose of an osmotic delivery system to deliver a defined concentration of beneficial agent at a fixed rate, both the start-up "burst" and the subsequent "lag" in delivery are undesirable.

A further aspect of an implantable, osmotically driven beneficial agent delivery system is that it is subject to external pressure or temperature changes (e.g., scuba diving, a hot bath, or temperature cycling during shipping) which may, in turn, result in transient spikes in the beneficial agent delivery profile.

It is possible with the current designs to develop high enough pressures within the implantable osmotic delivery device that one or more of the implant components fails or is expelled. In an effort to reduce the possibility of component failure or expulsion, previous designs have provided grooves in the reservoir walls and/or ribs in the semi-permeable membrane or holes in the wall of the device which are open if a component of the device moves out of position. These approaches add cost to the device by requiring additional machining to the part designs.

Accordingly, it is an objective of the present invention to minimize the start-up "burst" by containing the beneficial agent with a spring-loaded valve until the internal, osmotic-induced pressure is great enough to overcome the applied spring force, thereby opening the valve and allowing controlled release of the agent. It is also an objective of this invention that the post-start-up "lag" in beneficial agent delivery be minimized or eliminated as a further result of the elimination of the initial agent "burst." A further consequence of this minimization of start-up "burst" and post start-up "lag" is that the system may achieve the desired steady-state performance significantly sooner than in known implantable agent delivery devices.

Another objective of the present invention is to provide for the elimination of back-diffusion in a relatively inexpensive manner and without requiring a relatively large or long orifice, diffusion path, or exit channel.

An additional objective of the present invention is to provide an implantable osmotic delivery device capable of containing the total osmotic pressure that can develop within the device without requiring relatively expensive and sophisticated fluid flow bypass pathways.

BRIEF SUMMARY OF THE INVENTION

In accordance with the present invention, an implantable drug delivery system for use in mammals (preferably in humans) includes a capsule having an impermeable outer layer. The capsule has a beneficial agent delivery end and a fluid uptake end that are spaced apart from each other, but not necessarily located on opposite ends of the capsule. In addition, the capsule comprises a reservoir containing a beneficial agent; a movable dividing member separating the reservoir from the osmotic engine; and an osmotic engine. The delivery system includes a means for controlling beneficial agent flow through the beneficial agent delivery end that substantially prevents flow of beneficial agent out of the capsule when pressure within the capsule is above an upper predetermined pressure and prevents flow of fluid into the capsule through the beneficial agent delivery end when the pressure within the capsule is below a lower predetermined pressure. However, beneficial agent is substantially allowed to flow out of the capsule through the beneficial agent delivery end when the pressure within the capsule is between the lower and upper predetermined pressures.

In accordance with another aspect of the present invention, a device for dynamically regulating the flow of a beneficial agent from a pressurized beneficial agent delivery system includes a hollow body having a lower port and an upper port. The device also includes a means for controlling flow of interstitial fluid through the hollow body when pressure by the beneficial agent acting upon the means for controlling flow is below a lower predetermined pressure. The device also includes a means for controlling beneficial agent flow out of the device when the pressure in the device is above an upper predetermined pressure. The beneficial agent is substantially allowed to flow out of the device when the pressure in the device is between the lower and upper predetermined pressures.

According to a further aspect of the invention, a method of variably controlling the delivery of a beneficial agent from an implantable drug delivery system includes the steps of providing a capsule having a beneficial agent delivery end and a fluid uptake end, an agent reservoir containing a beneficial agent, an uptake reservoir containing a fluid attracting agent, and a movable dividing member between the agent reservoir and the uptake reservoir. The beneficial agent reservoir and the uptake reservoir are positioned adjacent the beneficial agent delivery end and the fluid uptake end, respectively. The method also includes the step of substantially preventing the flow of fluid into the capsule when a pressure within the capsule is below a lower predetermined pressure and flow of beneficial agent out of the capsule when a pressure within the capsule is above an upper predetermined pressure. The method still further includes the step of variably controlling the flow of the beneficial agent out of the capsule when the pressure is between the lower and upper predetermined pressures.

In accordance with yet another aspect of the invention, a method of variably controlling the delivery of a beneficial agent from an implantable osmotically driven delivery system includes the steps of displacing a movable closing member of a valve assembly with respect to a lower port via application of fluid pressure thereon from a beneficial agent reservoir to thereby create an opening between the closing member and the lower port. The method also includes the steps of increasing the size of the opening via increased pressure from the beneficial agent reservoir and allowing a beneficial agent from the beneficial agent reservoir to pass through the lower port and through the valve assembly. The method further includes the step of variably controlling the beneficial agent flow through the valve assembly such that the beneficial agent flow is directly proportional to the pressure applied by the beneficial agent against the movable closing member until the pressure approaches a predetermined maximum pressure, at which time the beneficial agent flow becomes more restricted as the pressure increases.

The present invention substantially prevents back-diffusion during the start-up phase by causing the spring-loaded valve to be closed during this time, effectively preventing fluid communication between the beneficial agent and interstitial fluids until the system is sufficiently pressurized, with the beneficial agent pumping at a sufficient rate, to disallow diffusion by the body fluid into the beneficial agent reservoir.

The present invention also provides the advantage of eliminating the need for a relatively long orifice, diffusion path or exit channel to prevent back-diffusion in an implantable osmotically driven delivery device.

In addition, the present invention provides an implantable osmotically driven delivery device which has the capability to withstand and contain the full system osmotic pressure, an especially critical consideration with any highly potent beneficial agent, without requiring relatively expensive and sophisticated fluid flow bypass pathways.

Furthermore, the present invention eliminates the need for and cost of a separate fluid bypass pathway.

BRIEF DESCRIPTION OF THE SEVERAL VIEWS OF THE DRAWINGS

The invention will be described in greater detail with reference to the accompanying drawings in which like elements bear like reference numerals, and wherein.

DETAILED DESCRIPTION OF THE INVENTION

The present invention relates to a pressure activated, two-way valve and self-adjusting flow channel for use in regulating fluid flow in an implantable osmotically driven beneficial agent delivery system. The components of the two-way valve and self-adjusting flow channel are designed to substantially prevent the passage of interstitial fluid therethrough when the pressure within a beneficial agent reservoir is below a lower predetermined pressure and prevent passage of beneficial agent therethrough when the pressure within a beneficial agent reservoir is above an upper predetermined pressure. This is accomplished by the narrowing of the fluid flow channel when the pressure within the beneficial agent reservoir is either below a lower predetermined pressure or above a higher predetermined pressure. At exceptionally high pressure, the valve can be designed to close altogether at the orifice end, or it can provide a minimal leak path so that a maximum fluid flow is never exceeded. At zero or very low pressures, the valve will close completely or provide a minimal leak path at the beneficial agent reservoir end, thereby substantially isolating the agent formulation from external fluid infiltration and eliminating diffusion of external fluid into the beneficial agent formulation. While these performance criteria can be achieved with various discrete components (e.g., relief valve, flow restrictor, check valve), this invention combines all the desired performance with a single, simple, and low cost mechanism.

While it is impractical to expect that external effects, such as external pressure or temperature changes, on the delivery system may be regulated or eliminated, the present invention minimizes the error contribution of them by requiring a significant increase in the overall pressure at which the system still dispenses beneficial agent. By forcing the system to pump or deliver beneficial agent at higher pressures, there is a reduction in overall variability of the pumping or delivery rate. As an example, a 0.01 psi (pounds per square inch) pressure increase will contribute substantially more error to a system dispensing at a nominal pressure of 0.10 psi than a 0.10 psi increase will to a system dispensing at 3 psi (10% vs. 3%).

Figure 1:
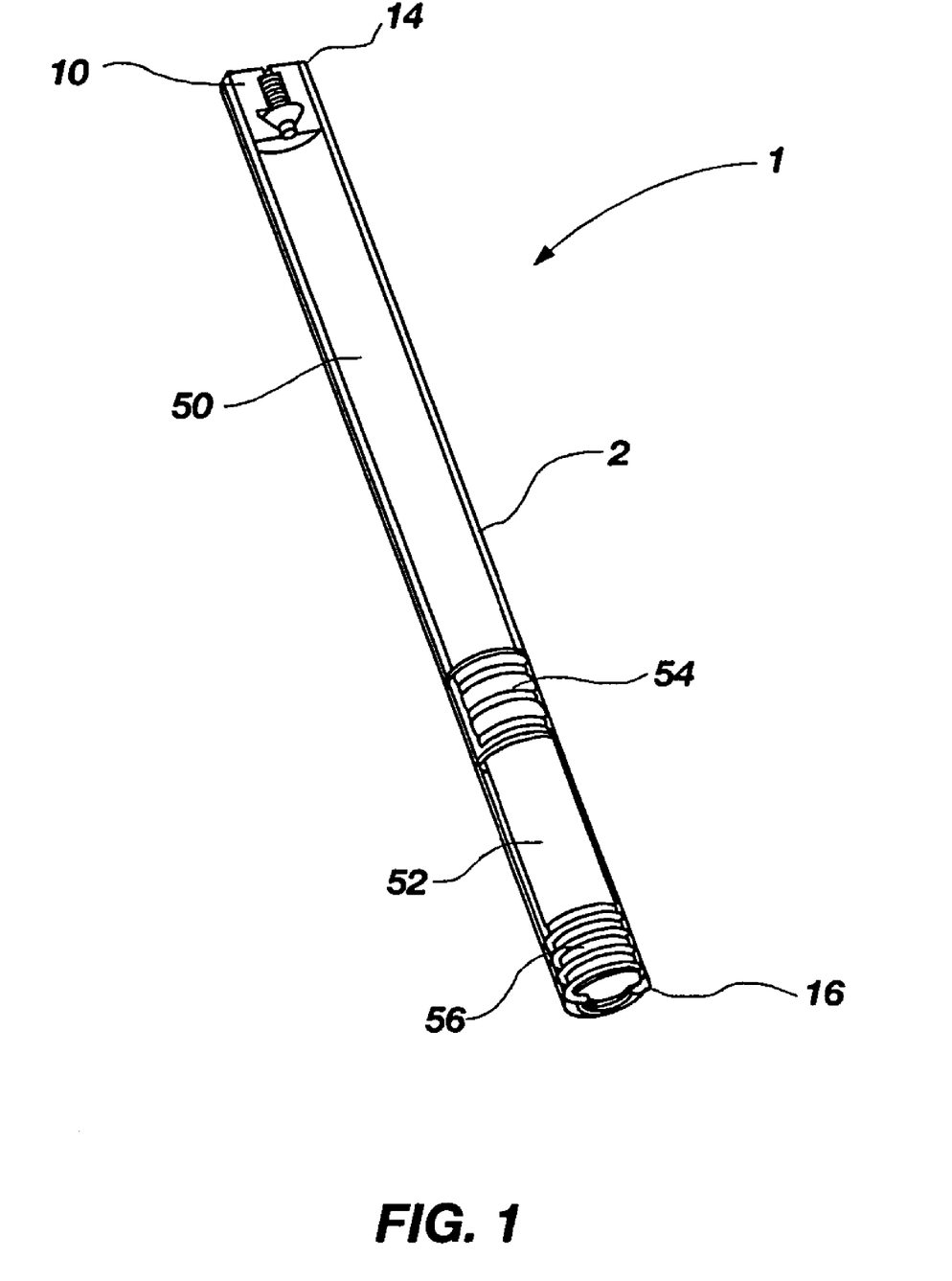
FIG. 1 is a cross-sectional side view of an osmotic agent delivery device including a two-way valve and a dynamically self-adjusting flow channel in a normal condition.

FIG. 1 illustrates an implantable osmotically driven beneficial agent delivery system 1 having a capsule 2. The capsule 2 has an impermeable outer layer and includes a beneficial agent reservoir 50 and an osmotic agent reservoir 52. The beneficial agent delivery system 1 also preferably includes a movable piston 54 positioned between the beneficial agent reservoir 50 and the osmotic agent reservoir 52. A fluid permeable membrane 56 is provided at the fluid uptake end 16 of the beneficial agent delivery system 1. The fluid permeable membrane 56 can be any suitable membrane or combination of membranes in a shape that can adequately control the amount of fluid entering into the capsule 2. Additionally, the membrane 56 should also be selected to prevent the compositions within the capsule 2 from passing out of the capsule. A valve assembly 10 is provided at the beneficial agent delivery end 14 of the capsule 2.

The capsule 2 must be sufficiently strong to ensure that it will not leak, crack, break, or distort so as to expel its beneficial agent contents under stresses it would be subjected to during use while being impermeable. In particular, it should be designed to withstand the maximum osmotic pressure that could be generated by the water-swellable osmotic agent in reservoir 52. Capsule 2 must also be chemically inert and biocompatible, that is, it must be non-reactive with the beneficial agent formulation as well as the body. Suitable materials generally comprise a non-reactive polymer or a biocompatible metal or alloy. The polymers include acrylonitrile polymers such as acrylonitrile-butadiene-styrene terpolymer, and the like; halogenated polymers such as polytetrafluoroethylene, polychlorotrifluoroethylene copolymer tetrafluoroethylene and hexafluoropropylene polyimide; polysulfone; polycarbonate polyethylene; polypropylene; polyvinylchloride-acrylic copolymer; polycarbonate-acrylonitrile-butadiene-styrene; polystyrene; and the like. The water vapor transmission rate through compositions useful for forming the reservoir are reported in *J. Pharm. Sci.*, Vol. 29, pp. 1634-37 (1970); *Ind. Eng. Chem.*, Vol. 45, pp. 2296-2306 (1953); *Materials Engineering*, Vol. 5, pp. 38-45 (1972); *Ann. Book of ASTM Stds.*, Vol. 8.02, pp. 208-211 and pp. 584-587 (1984); and *Ind. and Eng. Chem.*, Vol. 49, pp. 1933-1936 (1957). The polymers are known in *The Handbook of Common Polymers* by Scott and Roff, CRC Press, Cleveland Rubber Co., Cleveland, Ohio. Metallic materials useful in the invention include stainless steel, titanium, platinum, tantalum, gold and their alloys as well as gold-plated ferrous alloys, platinum-plated ferrous alloys, cobalt-chromium alloys and titanium nitride coated stainless steel. A reservoir made from titanium or a titanium alloy having greater than 60%, often greater than 85%, titanium is particularly preferred for most size-critical applications.

The osmotic agent reservoir 52 may contain any suitable osmotic agent, examples of which include, but are not limited to, a non-volatile water soluble osmagent, an osmopolymer which swells on contact with water, or a mixture of the two. Representative osmagents or osmopolymers are described, for example, in U.S. Pat. Nos. 5,413,572 and 6,270,787, which are hereby incorporated herein by reference. Osmotic agents, such as sodium chloride with appropriate lubricants, binders, and viscosity modifying agents, such as sodium carboxymethylcellulose or sodium polyacrylate can be prepared in various forms. Sodium chloride in tablet form is a preferred water swellable agent as described, for example, in U.S. Pat. No. 5,728,396, which is hereby incorporated herein by reference. The osmotic agent should be capable of generating between 0 and 5200 psi.

Materials for the fluid permeable membrane 56 are those that are semipermeable and that can conform to the shape of the reservoir upon wetting and make a water tight seal with the rigid surface of the reservoir. The semipermeable membrane expands as it hydrates when placed in a fluid environment so that a seal is generated between the mating surfaces of the membrane and the reservoir. The polymeric materials from which the membrane may be made vary based on the pumping rates and device configuration requirements and include, but are not limited to, plasticized cellulosic materials, enhanced polymethylmethacrylate such as hydroxyethylmethacrylate (HEMA) and elastomeric materials such as polyurethanes and polyamides, polyether-polyamide copolymers, thermoplastic copolyesters and the like. Further semipermeable compositions are described in U.S. Pat. Nos. 5,413,572 and 6,270,787, which are hereby incorporated herein by reference.

The movable dividing member can be of any shape that isolates the water-swellable agent from the beneficial agent formulation, including, but not limited to, a sheet or a piston 54. The movable dividing member isolates the water-swellable agent in reservoir 52 from the beneficial agent formulation in reservoir 50 and must be capable of sealably moving under pressure within capsule 2. The movable piston 54 is preferably made of a material that is of lower durometer than the capsule 2 and that will deform to fit the interior of the capsule 2 to provide a fluid-tight compression seal with the capsule 2. The materials from which the movable dividing member or piston is made are preferably elastomeric materials that are impermeable and include, but are not limited to, polypropylene, rubbers such as EPDM, silicone rubber, butyl rubber, and the like, fluoro elastomers, perfluoro elastomers, and thermoplastic elastomers such as plasticized polyvinylchloride, polyurethanes, Santoprene®, C-Flex® TPE, a styrene-ethylene-butylene-styrene copolymer (Consolidated Polymer Technologies Inc.) and the like. The movable dividing member, or movable piston, may be of a compression-loaded design.

Implantable drug delivery devices of this invention are useful to deliver a wide variety of active agents. These agents include, but are not limited to, pharmacologically active peptides and proteins, genes and gene products, other gene therapy agents, and other small molecules. The polypeptides may include, but are not limited to, growth hormone, somatotropin analogues, somatomedin-C, Gonadotropic releasing hormone, follicle stimulating hormone, luteinizing hormone, LHRH, LHRH analogues such as leuprolide, nafarelin and goserelin, LHRH agonists and antagonists, growth hormone releasing factor, calcitonin, colchicine, gonadotropins such as chorionic gonadotropin, oxtocin, octreotide, somatotropin plus an amino acid, vasopressin, adrenocorticotrophic hormone, epidermal growth factor, prolactin, somatostatin, somatotropin plus a protein, cosyntropin, lypressin, polypeptides such as thyrotropin releasing hormone, thyroid stimulation hormone, secretin, pancreozymin, enkephalin, glucagons, endocrine agents secreted internally and distributed by way of the bloodstream, and the like. Further agents that may be delivered include $\alpha_1$ antitrypsin, factor VIII, factor IX and other coagulation factors, insulin and other peptide hormones, adrenal cortical stimulating hormone, thyroid stimulating hormone and other pituitary hormones, interferon including, but not limited to, $\alpha, \beta,$ and $\delta$, erythropoietin, growth factors such GCSF, GMCSF, insulin-like growth factor 1, tissue plasminogen activator, CD4, dDAVP, interleukin-1 receptor antagonist, tumor necrosis factor, pancreatic enzymes, lactase, cytokines, interleukin 2, tumor necrosis factor receptor, tumor suppresser proteins, cytotoxic proteins, and recombinant antibodies and antibody fragments, and the like.

The above agents are useful for the treatment of a variety of conditions including, but not limited to, hemophilia and other blood disorders, growth disorders, diabetes, leukemia, hepatitis, renal failure, HIV infection, hereditary diseases such as cerebroside deficiency and adenosine deaminase deficiency, hypertension, septic shock, autoimmune diseases such as multiple sclerosis, Graves disease, systemic lupus erythematosus and rheumatoid arthritis, shock and wasting disorders, cystic fibrosis, lactose intolerance, Crohn's disease, inflammatory bowel disease, and gastrointestinal and other cancers.

The active agents may be anhydrous or aqueous solutions, suspensions or complexes with pharmaceutically acceptable vehicles or carriers such that a flowable formulation is produced that may be stored for long periods on the shelf or under refrigeration, as well as stored in an implanted delivery system. The formulations may include pharmaceutically acceptable carriers and additional inert ingredients. The active agents may be in various forms, such as uncharged molecules, components of molecular complexes or pharmacologically acceptable salts. Also, simple derivatives of the agents (such as prodrugs, ethers, esters, amides, etc.) which are easily hydrolyzed by body pH, enzymes, etc., can be employed.

Figure 2A:
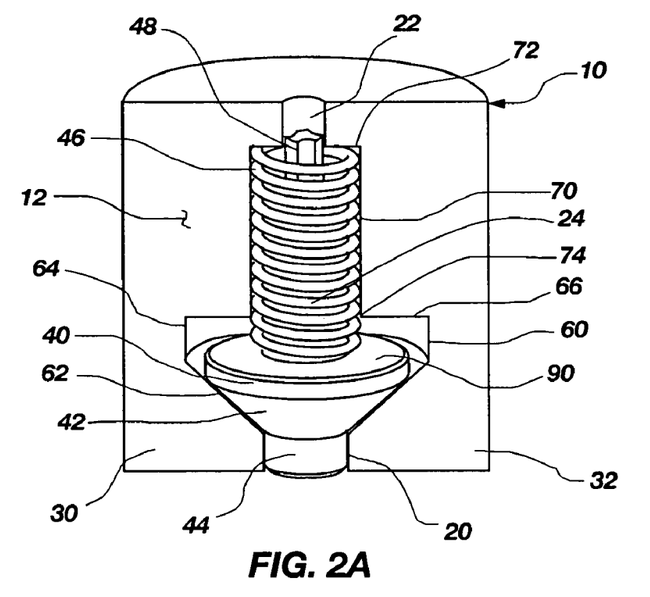
FIG. 2a is a cross-sectional side view of an upper section of an osmotic agent delivery device including a two-way valve and a dynamically self-adjusting flow channel, in which the closing member has been axially displaced.
Figure 2B:
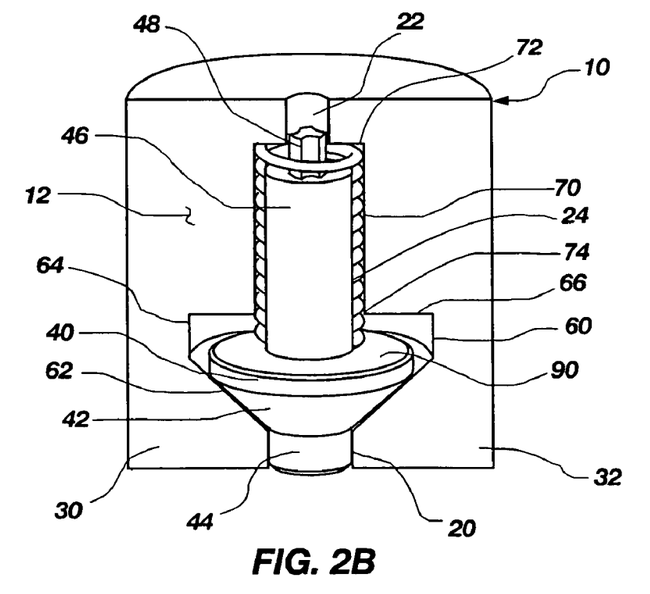
FIG. 2b is a cut away view of the valve shown in FIG. 2a, showing the elongated cylindrical stem.
Figure 3:
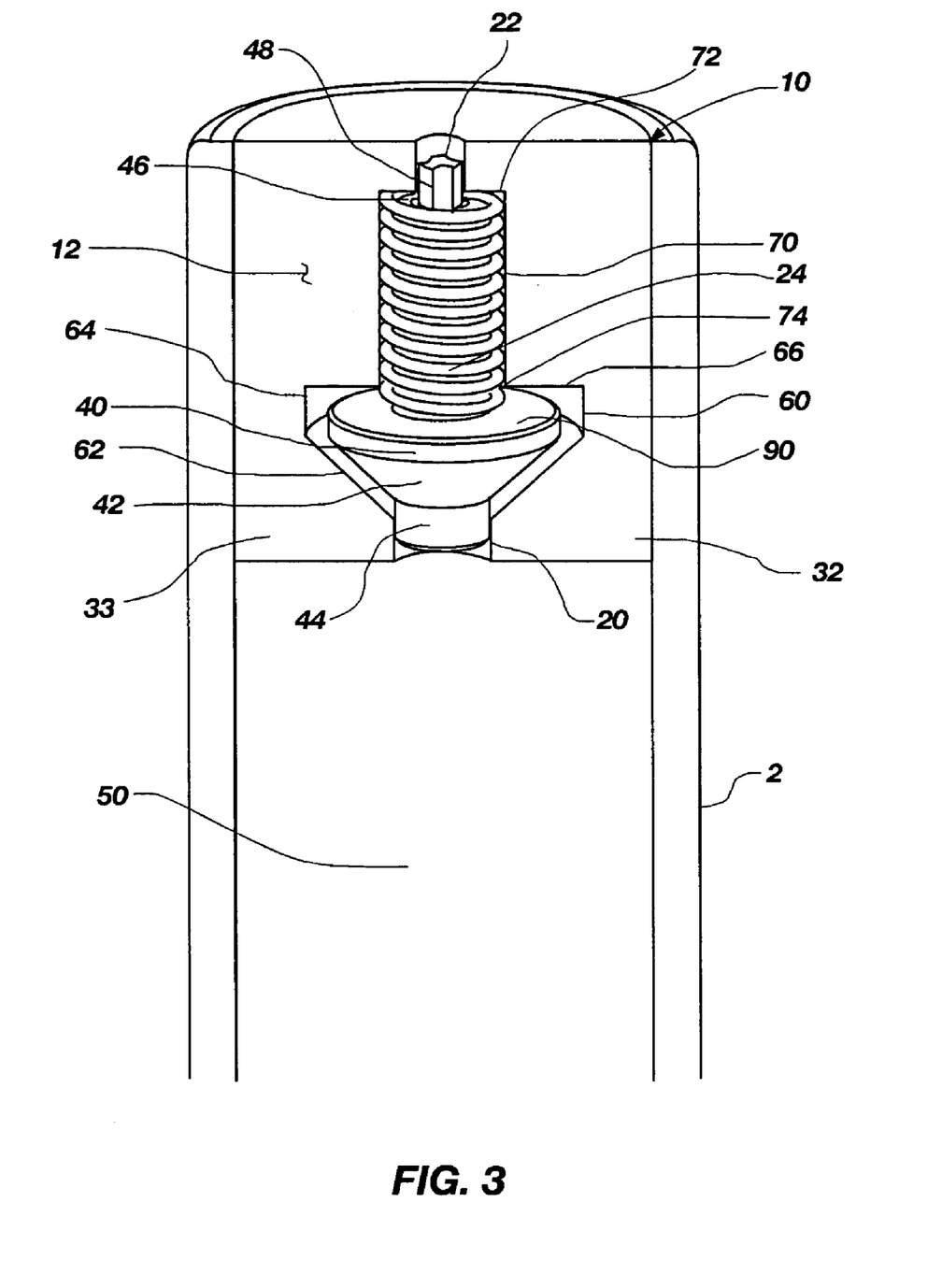
FIG. 3 is a cross-sectional side view of an upper section of an osmotic agent delivery device including a two-way valve and a dynamically self-adjusting flow channel, in which the closing member has been axially displaced to a greater extent than that shown in FIGS. 2a and 2b.

Referring now to FIGS. 2a and 2b, valve body halves 30 and 32 are preferably made of titanium, steel, and their alloys, thermoplastics including polyether ketone (PEEK) or liquid crystal polymers (LCP) and the like. More preferably valve body halves 30 and 32 are made of a liquid crystal polymer.

Spring 24 is preferably made of spring steels including stainless steel or beryllium/copper or injection molded polymer or plastic. The spring material should provide dimensionality while having a wire thickness that can be manufactured and inserted into the valve. More preferably spring 24 is made of stainless steel for a fine wire spring or a suitable plastic for a thicker wire spring. The profile of spring 24 may be round, square, or any other appropriate shape. Spring 24 provides the fluid path from reservoir 50 through upper port 22.

Stem 46 and guide post 48 may be made of the same materials as valve body halves 30 and 32, or elastomeric materials such as fluoro elastomers, perfluoro elastomers, thermoplastic elastomers such as C-Flex® or Santoprene®, hard plastics, or the like. Stem 46 and guide post 48 are preferably made of thermoplastic elastomers, perfluoro elastomers, or hard plastic.

In operation, fluid from the exterior of the capsule 2 passes through the membrane 56 and into the capsule 2. Some of the fluid is then absorbed by the osmotic agent in reservoir 52, thereby causing the osmotic agent to swell. As the osmotic agent swells, the increased volume thereof causes the movable piston 54 to push the beneficial agent housed in the beneficial agent reservoir 50 to be dispensed through the valve assembly 10 and into the patient's body (FIG. 1). However, the beneficial agent is only dispensed through the valve assembly 10 when the pressure within the capsule 2 is greater than a lower predetermined pressure. The mechanics of the valve assembly 10 will be described in greater detail below with reference to FIGS. 1-5.

As can be seen in FIGS. 1, 2a and 2b, the valve assembly 10 includes a valve body 12 containing a plurality of interconnected fluid chambers 60 and 70. The valve assembly 10 should have a height measurement larger than the diameter measurement. In other words, the ratio of the height to width of the valve assembly should be greater than 1:1. The height to width ratio of the valve assembly should be less than 1:5. Preferably the height to width ratio of the valve assembly is between 1:1 and 1:2. The valve assembly preferably has a diameter of about 1 to about 10 mm, more preferably about 3 to about 6 mm. The valve assembly preferably has a height of about 5 to about 10 mm.

The valve body 12 preferably includes two identical halves 30 and 32. The valve assembly 10 further includes a lower port 20 and an upper port 22. A lower fluid chamber 60 is positioned adjacent to and in fluid communication with the lower port 20. An upper fluid chamber 70 is positioned between and in fluid communication with the upper port 22 and the lower fluid chamber 60.

The lower fluid chamber 60 includes a first surface 62 having a conical frustum shape and a second surface 64 having a cylindrical shape. The diameter of the lowermost portion of the first surface 62 is smaller than the diameter of the lower port 20. The diameter of the uppermost portion of the first surface 62 is substantially the same as the diameter of the second surface 64. The lower fluid chamber 60 also includes a third surface 66 that is substantially perpendicular to the second surface 64.

A passageway 74, formed at the intersection of the third surface 66 and the upper fluid chamber 70, is provided between the upper and lower fluid chambers 70, 60. The diameter of the upper port 22 is substantially smaller than the diameter of the upper fluid chamber 70 and a top surface 72 (also substantially perpendicular to second surface 64) is provided therebetween.

As illustrated in FIGS. 2a and 2b, the valve assembly 10 contains a movable closing member 40 having a cylindrical seal 44 and a conical frustum 42 attached to an elongated cylindrical stem 46 (shown more clearly in FIG. 2b) and a guide post 48. Stem 46 is slightly smaller in diameter than spring 24. Guide post 48 should have a diameter slightly smaller than the diameter of upper port 22. The movable closing member 40 also includes a substantially flat upper surface 90. The closing member 40 and the cylindrical stem 46 may be fabricated as a single piece, preferably by molding, or they may be separately fabricated and attached in any known manner. Additionally, the stem 46 may be fabricated with a threaded end that is configured to mate with a threaded opening provided on the upper surface 90 of the closing member 40.

The movable closing member 40 can be moved from a lowermost position substantially adjacent the first surface 62 to an uppermost position substantially adjacent the third surface 66. The conical frustum 42 of the closing member 40 is shaped to substantially mate with the first surface 62 when the closing member 40 is in the lowermost position. Additionally, the upper surface 90 of the closing member 40 is also shaped to substantially cover the third surface 66 of the lower fluid chamber 60 when the closing member is in the uppermost position. When the movable closing member 40 is in either of the above described positions, the flow of beneficial agent from the beneficial agent reservoir 50 through the valve assembly 12 is substantially impeded.

A spring 24 is provided around the cylindrical stem 46 and between the top surface 72 and the upper surface 90. The spring 24 is preferably a helical compression spring and is shown as such in FIG. 1. However, it is to be understood that any other suitable spring may be used in place of the helical compression spring.

At zero or low pressures (0.5 to 10 psi, for example), such as can be expected during storage or initial pump startup, the spring 24 maintains the closing member 40 in a position to substantially prohibit fluid flow in either direction of the valve assembly 10. Cylindrical seal 44 prevents fluid flow across the lower port 20 such that there is substantially no fluid communication between any beneficial agent contained within the beneficial agent reservoir 50 and, once implanted, interstitial fluid present at the upper port 22. Further, as can be seen in FIG. 2, movable closing member 40 is designed to travel through some predetermined axial displacement while still maintaining a seal at lower port 20. This occurs because the cylindrical seal 44 has a height that is greater than the height of the lower port 20. This feature allows the valve assembly 10 to contain the increased agent formulation volume that results from thermal expansion upon implantation without the startup burst that occurs in many devices.

The pressure necessary to either keep valve assembly 10 in the closed position (as illustrated in FIGS. 2 and 4) or in an open position (as illustrated in FIG. 3) is dependent, for example, on the viscosity of the beneficial agent formulation; the desired rate at which the beneficial agent formulation is delivered from the system; the spring constant of spring 24; and/or the amount of room spring 24 takes up in valve assembly 10.

The psi (pounds per square inch) range from low to high pressure (from valve open to valve closed) needs to be very narrow, but could be anywhere in the range of about 0.1 to about 2000 psi. Preferably the range is about 0.5 to about 100 psi.

The valve assembly 10 is fabricated by positioning the helical compression spring 24 over the cylindrical stem 46 of the movable closing member 40. The assembly 10 is subsequently captured between the two valve body halves 30 and 32 with the conical frustum 42 and cylindrical seal 44 oriented to engage the first surface 62 of lower fluid chamber 60 and the lower port 20, respectively. The resulting assembly will cause the spring 24 to be under a compressive load, forcing the conical frustum 42 to seal against the first surface 62 at lower fluid chamber 60. Consequently, the valve assembly 10 is normally closed to fluid flow at the lower port 20. The body halves 30 and 32 can be sealed together in any of a number of ways known in the art. For example, using adhesives, ultrasonic welding, or mechanical mating.

FIG. 3 illustrates the valve operation once the fluid pressure at the lower port 20 exceeds the minimal value (for example, about 5 psi) as would be the case for normal operation. In this case, the movable closing member 40 will be displaced axially upward toward the upper port 22, creating an opening at the lower port 20 and allowing the beneficial agent from the beneficial agent reservoir 50 to be pumped through the lower port 20 then through, successively, fluid chambers 60 and 70, and finally exiting upper port 22. The cross-sectional area of the opening, and thus the fluid flow, is directly proportional to the pressure applied by the fluid against the movable closing member 40 until such time as the pressure begins to approach some predetermined maximum value. In this case, the valve action is reversed as the upper surface 90 of the closing member 40 approaches the third surface 66 of the lower fluid chamber 60.

The spring 24 defines a spiral fluid flow path through the upper fluid chamber 70. The spring 24 compresses as the movable closing member 40 is forced upward by the flowing agent. Consequently, as the fluid pressure inside the beneficial agent reservoir 50 and the chamber 60 increases, the lower port 20 opens more fully while the fluid flow path progressively narrows, thus becoming more restrictive. Normal flow will cause a balance between the opposing forces of the spring and the fluid pressure while low fluid flow will typically be completely impeded by the compression spring 24 causing lower port 20 to be closed by the movable closing member 40. On the other hand, high fluid flow will typically be substantially impeded by the upper surface 90 of the movable closing member 40 substantially closing off the passageway 74. Compression of spring 24 reduces the flow path between lower fluid chamber 60 and upper port 22.

Figure 4:
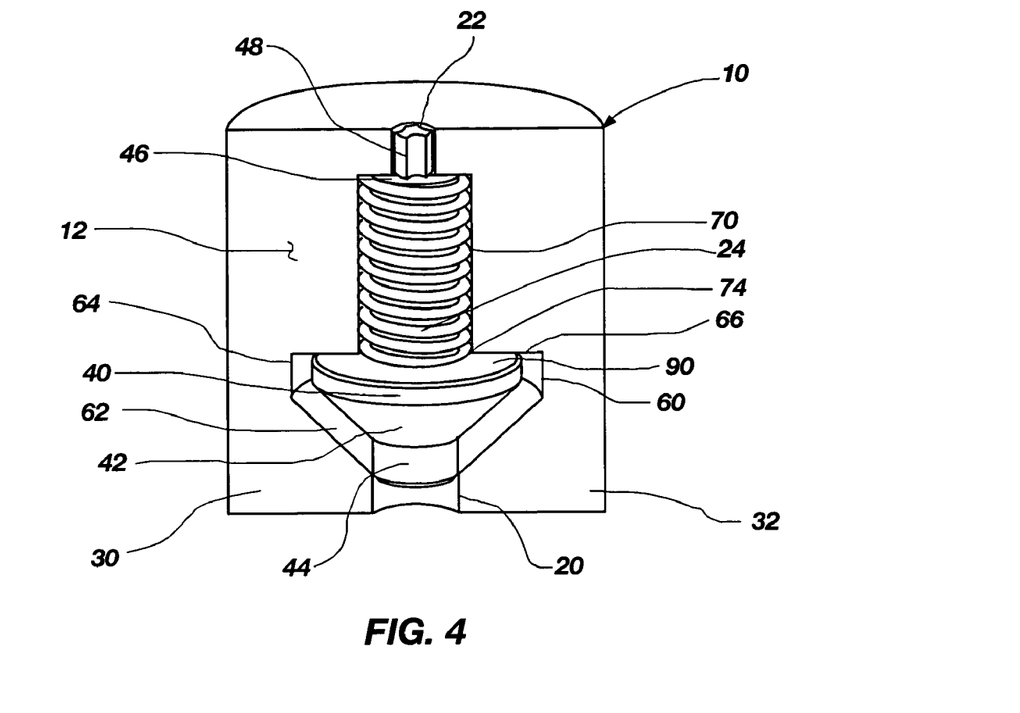
FIG. 4 is a cross-sectional side view of an upper section of an osmotic agent delivery device including a two-way valve and a dynamically self-adjusting flow channel, in which an upper chamber thereof is substantially closed off.

FIG. 4 shows the valve condition when a maximum pressure is reached (for example, about 20 psi). The movable closing member 40 has been driven in FIG. 4 to its uppermost position, forcing the movable member against third surface 66 of lower fluid chamber 60. This both limits the travel of the movable closing member 40 and either closes fluid communication between lower fluid chamber 60 and upper fluid chamber 70, or, in the preferred embodiment, limits the fluid flow around the movable closing member 40 to some predetermined minimal amount via a small fluid bypass channel around movable closing member 40. As the pressure is relieved, the fluid path increases in cross-sectional area at the third surface 66, thereby again allowing increased fluid flow. In this manner, fluid flow is continuously regulated to compensate for pressure and temperature variations, which would otherwise cause sub-optimal performance.

The above detailed description refers to a particular embodiment of the present invention. However, it should be obvious from the above disclosure that a broad range of materials, fabrication technologies, and alternative embodiments can be readily achieved. One further embodiment of this invention includes a separate small fluid bypass channel that can be formed by either a small hole through movable closing member 40 or a notch formed in one edge of movable closing member 40.

Figure 5:
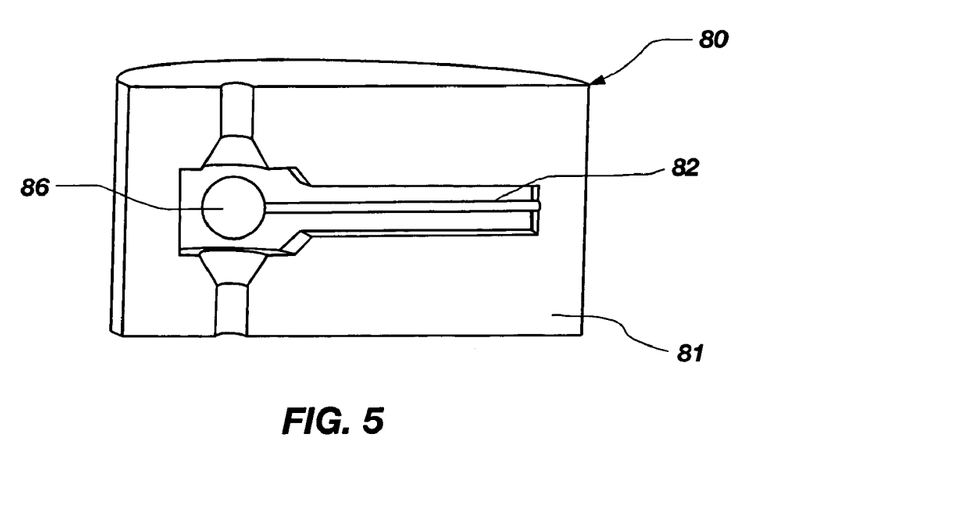
FIG. 5 is a cross-sectional side view of a two-way valve and a dynamically self-adjusting flow channel, according to a second embodiment of the invention.

As an example, FIG. 5 illustrates another preferred embodiment of the present invention, in which a valve assembly 80 can be fabricated as a silicon microstructure or molded in thermoplastic. As seen in FIG. 5, the valve assembly 80 includes a single chambered valve body 81 having an integrally formed cantilever spring arm 82 in place of the compression spring described hereinabove. The cantilever spring arm 82 may be made of metal (such as those described above for valve body halves 30 and 32) or a thermoplastic. Additionally, the movable closing member 86 is in the form of a spheroid and is attached to the free end of the cantilever spring arm 82. The movable closing member 86 may be made of a metal or metal alloy (such as those described above for valve body halves 30 and 32), a thermoplastic, or an elastomer. The upper and lower ports of this embodiment do not have to have the same diameter, as long as movable closing member 86 closes off the vertical portion of the upper or lower port when pressure is either lower or higher than a predetermined pressure. However, other shapes may also be used for the closing member 86. One potential benefit is that this embodiment presents an integral structure rather than an assembly and discrete components. Still another benefit is its extremely small overall size.

Furthermore, while the above description has described application to an osmotically driven agent delivery system in particular, it should be obvious that the present invention may be applied to any pressurized fluid delivery system.

The above-described exemplary embodiments are intended to be illustrative in all respect, rather than restrictive, of the present invention. Thus, the present invention is capable of many variations and detailed implementation that can be derived from the description contained herein by a person skilled in the art. All such variations and modifications are considered to be within the scope and the spirit of the present invention as defined by the following claims.

What is claimed is:

1. A device for dynamically regulating flow of a fluid from a pressurized fluid delivery system, the device comprising:
    a hollow body having a lower port and an upper port, wherein the hollow body comprises a closing member and a spring provided within the hollow body, wherein the spring comprises a cantilevered spring arm having two ends, one of the ends being attached to an inner surface of the hollow body, and further maintains the closing member in a position to substantially cover one of the lower and upper ports when the pressure acting upon the device by the fluid is below the lower predetermined pressure or above the upper predetermined pressure;
    wherein the closing member comprises a spherical member connected to the other end of the spring arm; and
    means for controlling fluid flow through the hollow body, the controlling means substantially preventing fluid flow when pressure acting upon the device by the fluid is below a lower predetermined pressure and when the pressure is above an upper predetermined pressure, and substantially allowing fluid flow when the pressure is between the lower and upper predetermined pressures.

2. The device according to claim 1, wherein the closing member includes an upper section, a middle section, and a lower section; the upper section having a cylindrical shape; the middle section having a conical frustum shape; and the lower section having a cylindrical shape which is smaller in diameter than the diameter of the upper section.

3. The device according to claim 1, wherein the hollow body comprises: an upper fluid chamber and a lower fluid chamber; the lower port being positioned adjacent the lower fluid chamber; and the upper port being positioned adjacent the upper fluid chamber.

4. The device according to claim 3, wherein the lower fluid chamber has a lower portion and an upper portion;
    the lower portion having a conical frustum shape and the upper portion having a cylindrical shape;
    the upper fluid chamber having a cylindrical shape,
    wherein the diameter of the upper portion of the lower fluid chamber is larger than the diameter of the upper fluid chamber;
    the lower fluid chamber having a substantially flat upper surface formed between the upper portion of the lower fluid chamber and the upper fluid chamber;
    wherein the closing member is housed within the lower fluid chamber;
    the middle section of the closing member being configured to matingly fit with the lower portion of the lower fluid chamber and the lower section of the closing member being configured to matingly fit within and substantially seal the lower port; and wherein the closing member has a substantially flat top surface having a diameter that is smaller than the diameter of the upper portion of the lower fluid chamber and larger than the diameter of the upper fluid chamber, such that the top surface of the closing member is capable of substantially blocking off fluid communication between the upper and lower fluid chambers when the closing member is in abutting relationship with the upper surface of the lower fluid chamber.

5. The device according to claim 3, wherein the spring comprises a compression spring and is positioned against a wall located between the upper port and the upper fluid chamber and applies force against the closing member to maintain the closing member against a lower section of the lower fluid chamber when the pressure is below the lower predetermined pressure.

6. The device according to claim 3, wherein when the pressure is above the upper predetermined pressure, the closing member substantially closes off fluid communication between the upper port and the lower fluid chamber.

7. The device according to claim 3, wherein when the pressure is between the lower and upper predetermined pressures, the closing member is maintained in a position substantially between the lower and upper ports.

8. The device according to claim 1, wherein the hollow body comprises a silicon microstructure.

* * * * *